United States Patent
Pollema et al.

[11] Patent Number: 5,849,592
[45] Date of Patent: Dec. 15, 1998

[54] CARRIERLESS SEQUENTIAL INJECTION ANALYSIS

[75] Inventors: Cy H. Pollema, Loveland; Daniel L. Campbell, Ft. Collins; Leon E. Moore, Windsor, all of Colo.

[73] Assignee: Hach Company, Loveland, Colo.

[21] Appl. No.: 864,747

[22] Filed: May 29, 1997

[51] Int. Cl.⁶ .............................. G01N 35/10; G01N 1/20
[52] U.S. Cl. .................. 436/52; 436/43; 436/174; 436/180; 422/68.1; 422/81; 422/52
[58] Field of Search .................. 436/43, 52, 53, 436/164, 174, 179, 180; 422/63, 68.1, 81, 82, 82.01, 82.03, 82.05, 100

[56] References Cited

U.S. PATENT DOCUMENTS

| | | | |
|---|---|---|---|
| 4,022,575 | 5/1977 | Hansen et al. | 422/100 |
| 4,315,754 | 2/1982 | Ruzicka et al. | 422/81 |
| 4,960,711 | 10/1990 | Aoki et al. | 436/124 |
| 5,019,515 | 5/1991 | Gisin et al. | 436/52 |
| 5,055,409 | 10/1991 | Astrom | 436/52 |
| 5,212,095 | 5/1993 | Miki et al. | 436/52 |
| 5,221,521 | 6/1993 | Hashizume et al. | 422/100 |
| 5,407,832 | 4/1995 | Hayashibe et al. | 436/74 |
| 5,573,651 | 11/1996 | Dasgupta et al. | 204/601 |

*Primary Examiner*—Long V. Le
*Attorney, Agent, or Firm*—Dean P. Edmundson

[57] ABSTRACT

A carrierless method is described for the analysis of a fluid sample for determination of the presence of a chemical species in the sample or for the determination of a physical characteristic of the sample. A portion of sample is drawn into a holding coil, followed by drawing one or more reagents (if desired) into the holding coil, then moving the sample and reagent (or reagents) through the reaction coil to a detector (e.g., calorimeter, potentiometer, ion selective electrode, fluorimetric detector, photometric detector, etc.). No separate carrier fluid is used in this method.

20 Claims, 5 Drawing Sheets

CARRIERLESS SEQUENTIAL INJECTION ANALYSIS

FIELD OF THE INVENTION

This invention relates to techniques and methods for analysis of liquids. More particularly, this invention relates to automated analysis of a moving liquid stream. Even more particularly, this invention relates to an improved automated analysis procedure which enables use of less reagent volumes than previous procedures.

BACKGROUND OF THE INVENTION

Flow injection analysis (FIA) refers to a family of analysis techniques originated by Jaromir Ruzicka in the early 1970's. The common principle behind all FIA methods involves a process of controlled dispersion of one liquid in a moving stream of another liquid. Dispersion is a process of diffusion and dilution which occurs in a narrow bore tubing.

Dispersion occurs during flow when a liquid plug of a single concentration is introduced into a flowing stream of a different concentration. During flow, the center portion of the fluid moves, on average, twice as fast as fluid near the walls of the tube. This allows the plug of fluid to penetrate into surrounding fluid. As this occurs, diffusion also dilutes the outer portions of the plug creating a gradient of concentrations which is highest at the center of the plug.

Another common factor in FIA methods is the reproducible operation which allows for accurate analysis in a short time. Previously, analytical methods most often allowed a reaction to go to completion to obtain accurate, comparable results. However, FIA does not allow enough time for a reaction to go to completion, but instead relies on the reaction progressing to the same extent for each analysis. Thus, since every portion of the sample handling occurs in the same manner, the signal produced by a set of standards creates a calibration line which accurately estimates an unknown sample concentration. Therefore, the reaction does not have to be complete if it is compared at a repeatable time. This was a significant improvement in automated analysis, since the time required to carry out an analysis dropped dramatically.

The first applications of FIA used only continuous, unidirectional flow. A plug or zone of sample was injected into a flowing stream of reagent and as the sample and reagent flowed, dispersion mixed them and created a detectable species. This species was measured as it flowed through a detector. This simple FIA system is illustrated in FIGS. 1A and 1B. The system consists of a pump, typically a peristaltic pump (PP), a two position injection valve (IV), a flow-through detector (D), and the various required connecting tubing. The reaction coil (RC) is the length of tubing connecting the valve and the detector. This component is varied depending on the chemistry being tested and the amount of dispersion required. Each component has certain requirements based on the theory of operation to obtain accurate and repeatable results. The pump has only to produce a constant flow rate in one direction. The valve needs to repeatably introduce a zone of sample. The detector needs to be low enough in dead volume to resolve the detectable species as it flows through the cell. Finally, the tubing has to maintain a constant inner diameter and defined flow properties. The sampling rate is determined by the dispersion and is limited to a minimum separation of sample to prevent carryover.

The steps in a typical analysis are sequentially shown in FIGS. 1A and 1B. First, sample is flowed through an injection loop to obtain well defined sample within the loop. This is the 'load' phase. Next, the valve is turned and the sample is introduced into the flowing stream of reagent. This is the 'inject' phase shown in FIG. 1B. The sample flows and disperses in the reagent stream and is detected as it passes through the flow cell.

Some of the advantages of FIA are high sample throughput, speed of analysis, a simple analytical system, low sample consumption, and high reproducibility. Some of the disadvantages are the high reagent consumption, and the increasing complexity of the system with chemistries which require multiple reagents. An illustration of a two and three reagent application is shown in FIGS. 2A and 2B where R1, R2 and R3 refer to separate reagent lines for different reagents and RC1 and RC2 are separate reaction coils. Increasing the number of required reagents is addressed by using merging points. Each reagent is driven by its own line. Results are best when a single peristaltic pump drives all reagents; however, tubing can still wear unevenly, leading to error. The peristaltic pump tubing is another distinct disadvantage of FIA. It is prone to wear out, it changes with time, and requires frequent maintenance. However, the basic operation of 'load' and 'inject' are still unchanged. Application of this traditional style of FIA technique remains the most popular and contributes the greatest number of publications within this field. Sequential injection analysis is still in its early development stage.

Sequential injection analysis (SIA) was developed at the University of Washington, under the direction of the Center for Process Analytical Chemistry (CPAC). The directive was to develop a simple, rugged form of FIA which was more geared towards process applications. SIA differs from FIA in many ways; however, the underlying principles of dispersion and reproducible fluid handling still hold true. SIA, however, introduced the idea of bidirectional noncontinuous flow of sample and reagent. The idea of stopping the flow was initially thought of as unique. See U.S. Pat. No. 4,315,754. The use of flow reversals had also been investigated in FIA for increasing mixing. SIA combined these points with the use of a single pump, single valve system. The requirements of the pump were greatly increased since now sample and reagent volumes were defined by aspiration by the pump, and these volumes needed to be repeatable for successful operation of a system. In FIA, these volumes were defined by lengths of tubing in the injection valve. In addition, the two position injection valve of FIA was replaced with a multiposition selector valve. The result was a system which could carry out complicated chemistries with a few rugged components. This created a system much more appealing to process applications.

The basic SIA system is illustrated in FIGS. 3A, 3B and 3C. The system consist of a syringe pump (SP), a multiposition valve (MPV), a flow-through detector (D), a reaction coil (RC), and a holding coil (HC). The requirements of the system are increased. The pump now has to be able to flow repeatably in both directions and stop. The resolution of the pump also needs to be high enough to repeatably aspirate the required volumes of sample and reagent, while maintaining an overall volume sufficient to flush the sample and reagent zones through the detector. The valve is a multiposition style and should introduce flow in the same manner regardless of the port position selected. Both components should be able to operate under computer control to control the timing of the required operations. The detector requirements are essentially unchanged as are those of the reaction coil. However, a holding coil has been added to the system. The purpose of the holding coil is to prevent reagents and sample from being aspirated into the pump and provide a defined volume in which to stack the sequential zones used in the analysis.

The method of analysis is illustrated also in FIGS. 3A, 3B and 3C. There are essentially three steps to the method. The first being to fill the system with a carrier solution C (FIG. 3A). This solution is typically DI water. The function of the carrier is to provide an inert solution to move the necessary sample and reagents through the system. The next step is to aspirate small zones of samples and the reagent (or reagents) R required for the analysis (FIG. 3B). This stack of zones is then dispensed to the detector in the third and final step (FIG. 3C) which disperses the zones and measures the species formed as the zones merge and pass through the detector. The theory of operation is essentially the same as FIA with regard to dispersion and reproducible handling. However, the sequential stack of zones and the optimization to get these zones to properly overlay is unique. Several papers have been published on the best ratios of zone volumes for different conditions. Up to six zones have been successfully handled in a chemistry which still could be performed with a single pump, single valve system. Therefore, increasing the number of reagents does not change the required components as it does in FIA, and there is an advantage over a comparable FIA system which would have required six different lines and six merging points. One pump probably would not be sufficient to deliver that number of reagents in an FIA system.

The advantages of SIA over FIA are the few components needed which are capable of handling a wide variety of applications, the low sample and reagent consumption, the ability to optimize and adjust a chemistry without replumbing, and the added flexibility brought on by utilizing flow in both directions. The disadvantages are the added sophistication of components required to operate in an SIA mode, which typically results in the need for computer control, and when addressing process applications, the large volume of carrier fluid required for operation. This volume is typically 40–50 times greater than the reagent consumption.

There has not heretofore been described an analysis system having the advantages and features provided by the present invention.

SUMMARY OF THE INVENTION

In accordance with the present invention there is provided a carrierless sequential injection analysis procedure or method which overcomes the main disadvantages and inherent limitations of conventional flow injection analysis and sequential injection analysis techniques. Using the technique and procedure of this invention, only the sample itself and the required reagents are used in the testing. No separate carrier fluid is used. This greatly simplifies the testing procedure and it also reduces the costs.

Carrierless sequential injection analysis (CSIA) retains the advantages of SIA including a minimal number of rugged components to carry out a wide variety of chemistries. CSIA also avoids many of the potential disadvantages of using a carrier solution in an analysis.

Use of the CSIA technique provides several advantages such as elimination of a carrier solution (typically over 40 liters per month in many testing situations). Because no carrier solution is required, there is no need for an extra port position to hold the carrier, and there is no concern with potentially contaminating the carrier solution which would lead to erroneous results. Also, the CSIA technique uses larger volumes of the sample, filling the system, whereas the SIA technique uses small zones of sample. There are several practical problems with the SIA approach. First, if the viscosity of the sample changes, the aspirated volume may change which on a small zone would significantly change the results. Also, the need to provide representative sample to the analyzer usually requires a separate 'flush' cycle to get sample to the valve head. The volumes with CSIA are reasonable to provide representative sample without requiring a discreet 'flush' cycle and large enough that changes in viscosity would not have the same effect. Yet, overall, the advantage of CSIA is simply in eliminating the carrier which eliminates many of the problems detailed above.

Other advantages and features of the analysis system of this invention will be apparent from the following detailed description and the accompanying drawings.

BRIEF DESCRIPTION OF THE DRAWINGS

The invention is described in more detail hereinafter with reference to the accompanying drawings, wherein like reference characters refer to the same parts throughout the several views and in which.

DETAILED DESCRIPTION OF THE INVENTION

Figure 1A:
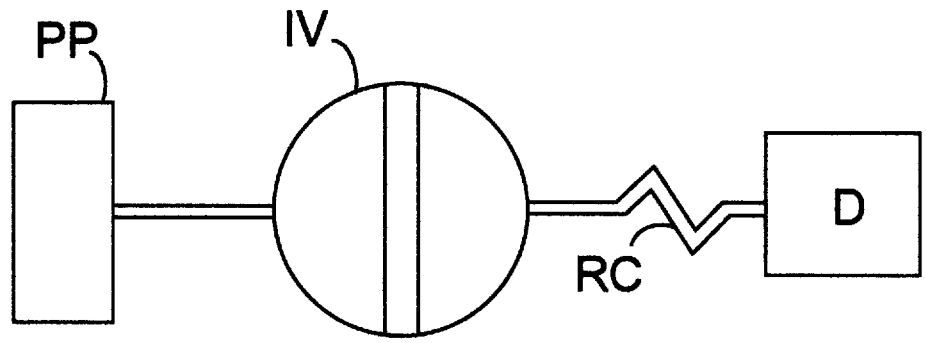
FIGS. 1A and 1B illustrate a conventional flow injection analysis system.
Figure 1B:
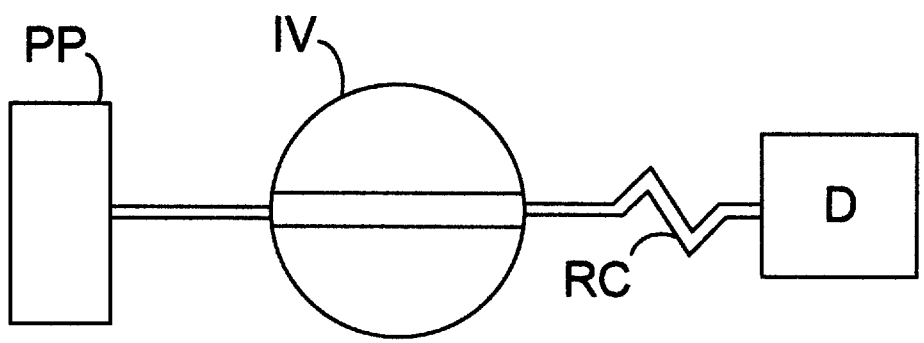
Figure 2A:
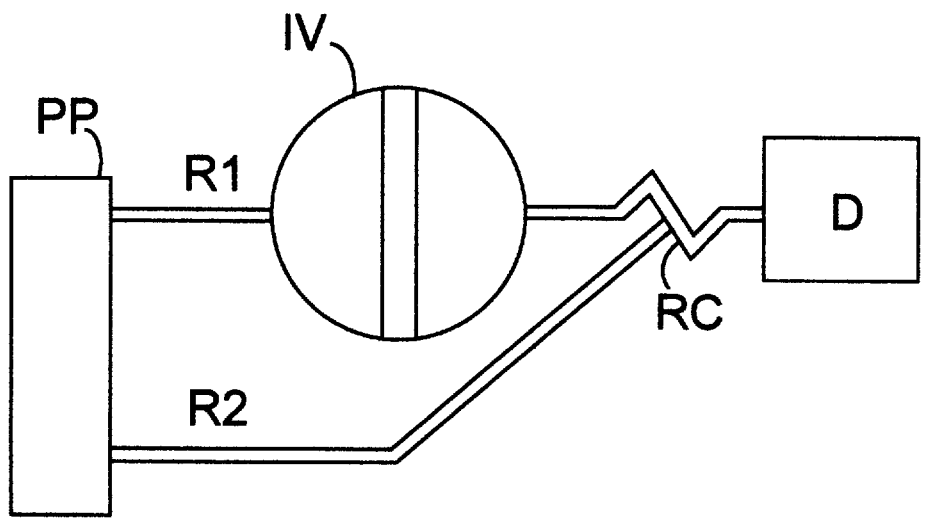
FIGS. 2A and 2B illustrate a conventional flow injection analysis system where more than one reagent is being used.
Figure 2B:
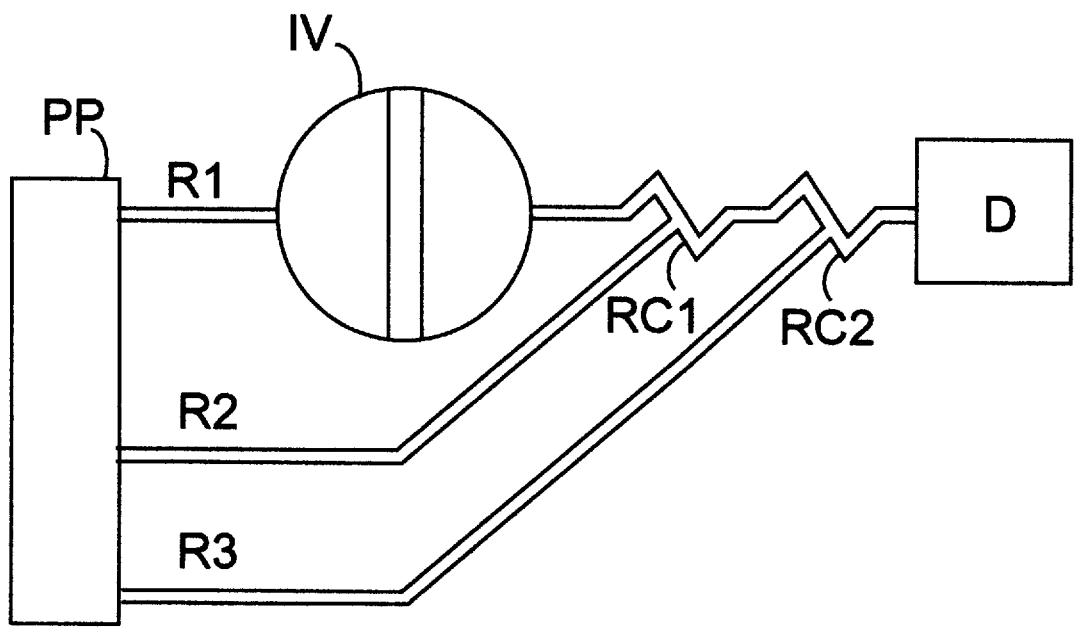
Figure 3A:
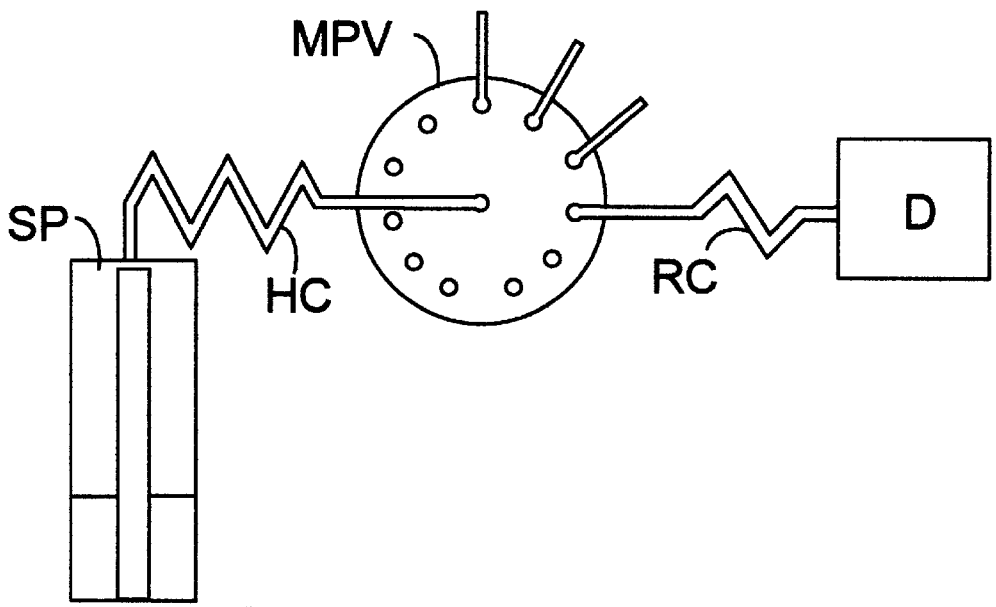
FIGS. 3A, 3B and 3C illustrate a conventional sequential injection analysis system.
Figure 3B:
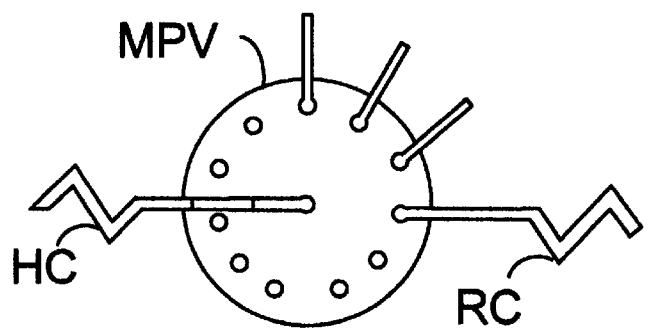
Figure 3C:
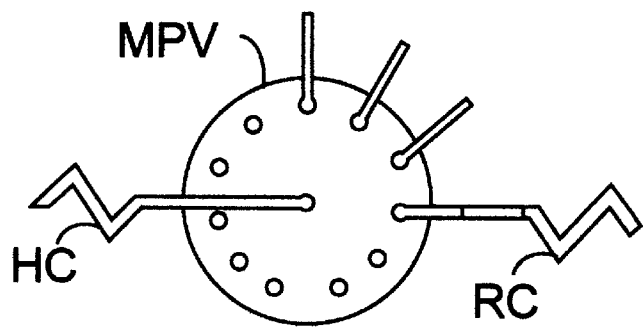
Figure 4A:
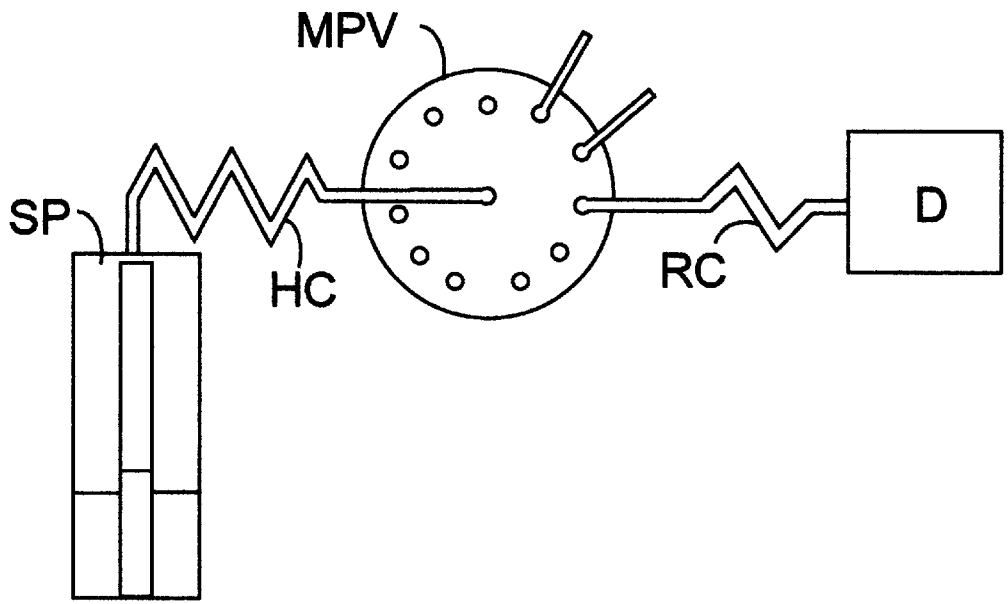
FIGS. 4A, 4B and 4C illustrate the carrierless sequential injection analysis system of this invention.
Figure 4B:
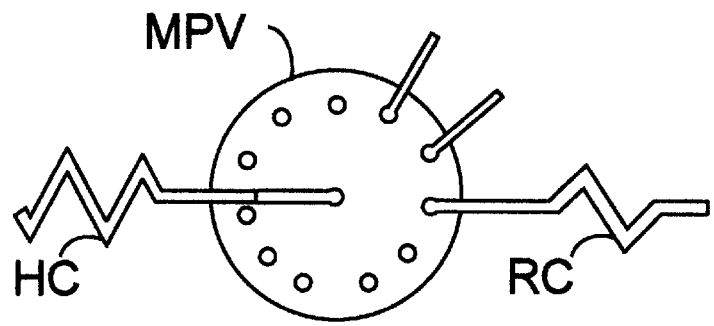
Figure 4C:
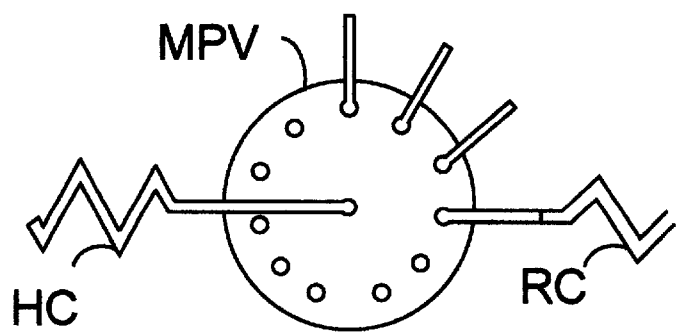

In the carrierless sequential injection analysis system of this invention the use of a separate carrier solution is wholly avoided. Only the liquid sample to be tested and the necessary reagents are required in the technique of this invention. This is illustrated in FIGS. 4A, 4B and 4C.

The first step is to fill the system through the valve (MPV) with representative sample(s) using a pump (SP). Several parameters affect the exact steps required to assure the system is filled with representative sample; however, in general, the full pump capacity is used to aspirate sample. Some portion of this sample is sent to the reaction coil to place representative sample in the reaction coil, and finally, the pump is once again filled to capacity from the sample line. Next, the reagent (or reagents) (R) are aspirated and, finally, the sample and reagent (or reagents) are dispensed to the detector through the reaction coil (RC).

The holding coil (HC) must be of a low dispersion type so that representative sample can be provided to the reagent zones in each analysis. In SIA, zones of liquid typically only travel 100–200 $\mu$L into the holding coil, and the only purpose of the holding coil is to prevent these zones from entering the poorly defined flow volume of the pump. Therefore, the dispersion properties of this conduit are not critical. However, in CSIA, representative sample needs to be provided in every cycle. The holding coil serves as the method of separating the old from new sample. The lower in dispersion this holding coil is, the less volume is required to get representative sample, and the more representative is the sample which is available for the analysis. Therefore, a controlled dispersion design for the holding coil is important to successful operation.

The significant change in using sample throughout the system and eliminating the carrier liquid is that the sample changes with each analysis, and thus the operation must be such that representative sample is provided to the reagent (or reagents) in each cycle while all the zones are moved with sample.

The pump must not contaminate the sample and therefore it should be made of components which are inert.

Because the entire holding coil becomes filled with sample, the portion of the sample in contact with reagent (or reagents) during an analysis must not be contaminated with carryover from any sample which previously filled the system. Therefore, in the analysis system of this invention the holding coil should have well-defined, controlled dispersion properties and an appropriate volume.

Figure 5A:
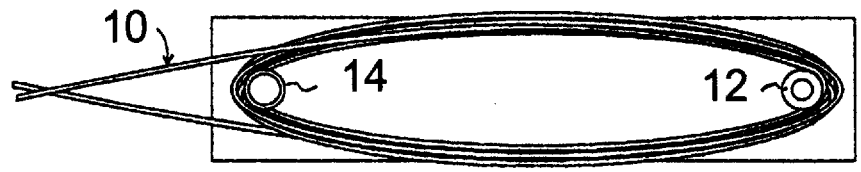
FIGS. 5A, 5B and 5C show the manner in which a preferred type of holding coil is produced for use in the techniques of this invention.
Figure 5B:
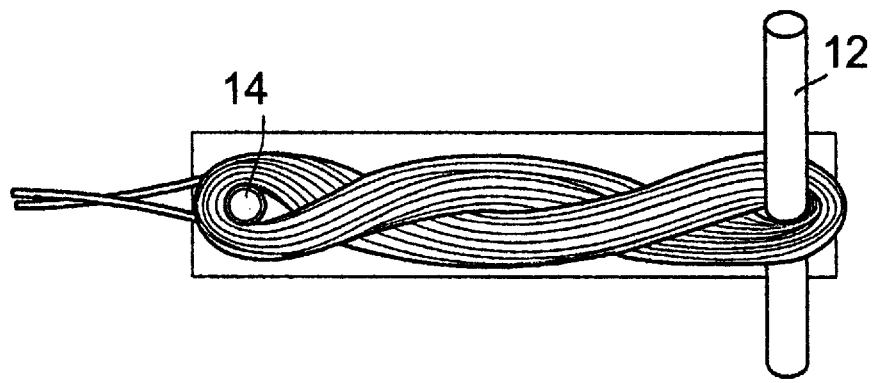
Figure 5C:
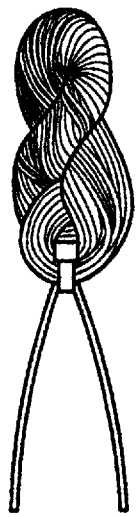

A number of different configurations may be used for the holding coil, e.g., serpentine, knitted or wrapped tubing. A preferred configuration for easy manufacture which was developed for use in this invention is twisted. This style is illustrated in FIGS. 5A, 5B and 5C and involves taking a given length of tubing 10 and wrapping it around a fixture with prongs 12 and 14 after which one of the prongs 12 is removed from the fixture and twisted or rotated while it holds the tubing. The opposite ends of the resulting structure are then tied together (FIG. 5C). This creates a tight spiral within a section of wrapped tubing. The end result is a controlled dispersion holding coil. However, the serpentine design still provides lower dispersion.

The volume and inner diameter of the holding coil are also important. The holding coil volume must be less than the volume of the pump to allow air to purge from the system during routine measurement. Yet, the volume should be maximized to create the largest possible zone of defined sample. Experimentally, it was determined that a holding coil volume which is 0.7 times the pump volume works well, although a holding coil volume which is 0.95 times the volume of the pump also was workable. The inner diameter must be large enough such that excess vacuum is not created during aspiration but small enough to minimize dispersion.

The requirements of a pump for use in the system of this invention are the ability to flow in both directions repeatably and stop, high enough resolution to aspirate low $\mu$L quantities, a large enough overall volume to provide representative sample around the reagents as they pass through the detector, inert components to allow sample in the pump body without adding contaminants, and finally, the ability to operate under computer control or in some other manner allow the necessary timing. Both peristaltic and syringe style pumps may meet these requirements. Peristaltic pumps have the advantage of being able to flow an 'infinite' volume in either direction, but the drawbacks focus mainly on the peristaltic tubing and the maintenance required. Syringe pumps are more accepted for process applications, but have a fixed pump volume and the piston seals also require maintenance.

It is desirable to minimize the application of vacuum when aspirating sample. This is necessary to minimize the outgassing of sample and creation of bubbles which interfere with repeatable results. Both samples and reagents are preferably maintained at a slight head pressure to avoid outgassing. In addition, samples can be applied to the system under pressure to eliminate creating any vacuum during aspiration. However, aspiration rates are typically limited to 2 mL/min to minimize this effect. In certain applications, backpressure devices are placed downstream of the detector to further eliminate outgassing of sample during analysis. All system components are also designed to not trap or retain air bubbles. This combination of steps has minimized the problem of air bubbles to less than 5% under adverse conditions. Other applications of FIA and SIA do not have this consideration since only small volumes of sample are introduced into the system.

The operating conditions for the analysis system of this invention, given the components and general guidelines listed above, are as follows. First, the fraction of representative sample which can be dispensed through the holding coil on a full pump stroke needs to be established. This can be experimentally determined by first filling the system with a clear solution, then aspirating a full pump stroke of a dye in place of sample. This volume is then dispensed through a minimal volume reaction coil and detector. The dye will create a steady state absorbance and maintain it for some fraction of the pump stroke until it begins to be diluted by the portion of clear solution which previously resided in the holding coil. The fraction of the full pump stroke in which the absorbance was not changed represents the amount of representative sample which is delivered through the holding coil. Next, an appropriate volume of reaction coil is added, the system is again thoroughly flushed and cleared with a clear solution and the same experiment repeated. Now, the fraction of the pump stroke which is required to attain a steady state absorbance is monitored. This represents the amount of sample required to flush the reaction coil. Given these two experiments, a 'window' of representative sample is created. The analysis needs to be developed to place the reagent (or reagents) within this window. The window can be broadened using multiple pump strokes and preloading the reaction coil.

The number and volume of reagents as well as the relative volumes of the reaction and holding coils will vary depending on the specific type of analyses; however, the general principle of using sample throughout the system, assuring representative sample in the analysis window, and allowing reproducible fluid handling as well as dispersion is universal in this method. This method can be applied to a broad range of applications using a variety of detection methods and fluidic handling approaches. Some examples of this are as follows:

EXAMPLE 1

The determination of water hardness uses a low volume flow-through calorimetric detector, a positive displacement syringe pump, a multiposition valve, a reaction coil and a holding coil. The first step is to fill the system (as illustrated in FIG. 4A) with the representative sample to be analyzed. The general procedure for this has been described above and, as outlined, a portion of the sample is dispensed to the reaction coil and the pump refilled with fresh sample. Next, the reagents (pH=11 buffer and calmagite indicator) are aspirated into the holding coil (see FIG. 4B). The valve is next turned back to the sample stream and the reagent zones are pulled further into the holding coil (HC) which improves mixing of the reagents and sample. Finally, the sample and reagents are dispensed to the detector through the reaction coil (see FIG. 4C). The calorimeter records the absorption value which is directly related to the concentration of hardness.

Calibration of the instrument if fully automatic using external standards. Known hardness standards are aspirated into the instrument and analyzed precisely the same as the samples. Based upon the external calibration, the concentration of the unknown sample is calculated.

A grab sample port is available on the instrument for quality control/quality assurance samples. It also provides for measurements of any samples taken from a remote site for rapid analysis. The sample is collected in a 10–20 mL vessel which attaches to an external sampling port on the front of the instrument. A simple press of a button initiates the sampling procedure, again identical to the sampling procedure described above. When the analysis is completed, a displayed value of the sample concentration is directly displayed on the instrument panel.

EXAMPLE 2

The determination of nitrate, ammonium, or sodium can be carried out with the present invention using an electrochemical approach. An ion selective electrode can be operated in a wall-jet style flow-through cell to measure the parameter of interest. In this example, CSIA can be utilized to simply introduce an ionic strength adjuster with the sample, allowing potentiometric monitoring, or this technique could introduce a second zone containing a standard to allow for a standard additions approach as the sample, standard and ionic strength adjuster disperse and mix in the reaction coil and detection cell. A typical method of analysis for these parameters would be to first obtain representative sample within the system (much like the previous calorimetric example), then aspirate small volumes of the ionic strength adjuster and standard as low volume zones. These zones would be propelled through a minimal volume reaction coil to obtain low dispersion, and passed through the detection cell. Multiple standards could be used in consecutive runs to automate the multiple standard addition approach which would correct for electrode drift and some temperature sensitivity.

EXAMPLE 3

The determination of alkalinity can also use a calorimetric detection approach, but bases quantitation on a titrametric approach. Now, rather than using peak height, peak width is used. Many of the basic steps are still the same; however, given that this method does use peak width, extra lengths are taken to achieve a broad window of representative sample. This is done by repeating the steps of filling the system with sample. This window determines the range of analyses. Finally, a zone of acid is introduced and the mixture of acid and sample are sent through the reaction coil. Several flow reversals are used at this stage to improve mixing. A second pump is used to slowly meter a constant fraction of indicator into the reaction coil just prior to the detector. The indicator changes absorbance based on pH to create a detectable signal at the calorimetric detector. A wide peak indicates little ability of the sample to titrate the acid, and thus would be a low alkalinity, a narrow peak would result if the sample could titrate the acid reagent, indicating a high concentration of alkalinity.

EXAMPLE 4

The determination of nickel is yet another example of the use of CSIA with a fluorimetric detection approach. As with the other methods, representative sample is first introduced into the analyzer and the holding and reaction coils are flushed. Next, the sample is mixed with an aluminum-PAN ([1-2-pyriddylazo)-2-naphthol]) reagent. As the sample and reagent mix, the nickel is complexed by the PAN and aluminum is released. The aluminum PAN complex fluoresces, but the nickel PAN does not. Therefore, the concentration of nickel can be determined by the drop in fluorescence.

EXAMPLE 5

In addition, the determination of sulfate may be carried out by its quantitative precipitation with barium chloride. In solution, this finely-divided barium sulfate forms a proportional relationship with sulfate and turbidity. A photometric reading enables the sulfate concentration to be determined accurately. The determination of sulfate by turbidity would use a low-volume flow-through photometric detector similar to that described in the calorimetric examples described above. In this example, the reagent (barium chloride) is aspirated into the sample. The reagent will cause a milky precipitate to form if sulfate is present. Next, the sample and reagent zones are dispensed to the detector through the reaction coil. The photometric detector records the absorption value which is directly related to the concentration of sulfate.

EXAMPLE 6

The determination of ozone uses a low volume flow-through Ultra-Violet detector (D), a positive displacement syringe pump (SP), a multiposition valve (MPV), a reaction coil (RC) and a holding coil (HC). All wetable parts in the analyzer are constructed of inert polymeric material resistant to ozone and chemical attack. The analysis of ozone in water at ppm and sub-ppm levels has presented a difficult challenge for chemists for many years. This difficulty has limited the study of the applicability of ozonation to water. The instability of ozone in water has often been discussed in literature and most analytical methods for this gas in water has involved low pH solutions and temperatures near the freezing point of water. In the method of this invention, a sample is rapidly aspirated with the sample pump (SP) filling the system with sample. The multiposition valve is actuated and the sample is dispensed to the detector through the reaction coil. In this application, the detector is a conventional ultraviolet detector which directly measures ozone concentration in the sample with minimal handling.

Other variants are possible without departing from the scope and intent of this invention.

What is claimed is:

1. A carrierless method for analyzing a fluid sample for determination of the presence of a chemical species therein, the method comprising the steps of:
   (a) providing a pump operatively connected to a multiposition valve, a holding coil, a reaction coil, and a flow-through detector;
   (b) drawing said sample through said valve and into said holding coil;
   (c) drawing at least one reagent into said holding coil through said valve;
   (d) moving said sample and reagent through said reaction coil to said detector in the absence of a separate liquid carrier.

2. A method in accordance with claim 1, wherein said holding coil comprises a controlled dispersion coil.

3. A method in accordance with claim 2, wherein said dispersion coil comprises a length of tubing which has been wrapped and twisted.

4. A method in accordance with claim 1, further comprising the steps of dispensing a portion of said sample from said holding coil to said reaction coil and then re-filling said holding coil with additional sample.

5. A method in accordance with claim 1, wherein said detector comprises a colorimeter.

6. A method in accordance with claim 1, wherein said detector comprises a potentiometer.

7. A method in accordance with claim 1, wherein said detector comprises an ion selective electrode.

8. A method in accordance with claim 1, wherein said detector comprises a fluorimetric detector.

9. A method in accordance with claim 1, wherein said detector comprises a photometric detector.

10. A method in accordance with claim 1, wherein said sample is aqueous.

11. A carrierless method for analyzing a fluid sample for determination of a physical property of said sample, the method comprising the steps of:

(a) providing a pump operatively connected to a multi-position valve, a holding coil, a reaction coil, and a flow-through detector;

(b) drawing said sample through said valve and into said holding coil;

(c) moving said sample through said reaction coil to said detector in the absence of a separate liquid carrier.

12. A method in accordance with claim 11, wherein said holding coil comprises a controlled dispersion coil.

13. A method in accordance with claim 12, wherein said dispersion coil comprises a length of tubing which has been wrapped and twisted.

14. A method in accordance with claim 11, further comprising the steps of dispensing a portion of said sample from said holding coil to said reaction coil and then re-filling said holding coil with additional sample.

15. A method in accordance with claim 11, wherein said detector comprises a calorimeter.

16. A method in accordance with claim 11, wherein said detector comprises a potentiometer.

17. A method in accordance with claim 11, wherein said detector comprises an ion selective electrode.

18. A method in accordance with claim 11, wherein said detector comprise a fluorimetric detector.

19. A method in accordance with claim 11, wherein said detector comprises a photometric detector.

20. A carrierless method for analyzing a liquid sample for determination of the presence of a chemical species therein, the method comprising the steps of:

(a) providing a pump operatively connected to a multi-position valve, a holding coil, a reaction coil, and a flow-through detector;

(b) drawing said sample through said valve and into said holding coil (c) drawing at least one reagent into said holding coil through said valve; and (d) moving said sample and reagent through said reaction coil to said detector in the absence of a separate liquid carrier.

* * * * *